US00PP21715P2

(12) United States Plant Patent
Drewlow

(10) Patent No.: US PP21,715 P2
(45) Date of Patent: Feb. 15, 2011

(54) POINSETTIA PLANT NAMED 'OGLPNT14001'

(50) Latin Name: ***Euphorbia pulcherrima* Willd.**
Varietal Denomination: OGLPNT14001

(75) Inventor: Lyndon Wayne Drewlow, Lompoc, CA (US)

(73) Assignee: The Paul Ecke Ranch, Encinitas, CA (US)

( * ) Notice: Subject to any disclaimer, the term of this patent is extended or adjusted under 35 U.S.C. 154(b) by 3 days.

(21) Appl. No.: 12/462,572

(22) Filed: Aug. 5, 2009

(51) Int. Cl.
*A01H 5/00* (2006.01)

(52) U.S. Cl. ..... Plt./305

(58) Field of Classification Search ..... Plt./305, Plt./304
See application file for complete search history.

*Primary Examiner*—June Hwu
(74) *Attorney, Agent, or Firm*—C. A. Whealy

(57) ABSTRACT

A new and distinct cultivar of Poinsettia plant named 'OGLPNT14001', characterized by its uniform, upright, outwardly spreading and mounded plant habit; vigorous growth habit; freely branching habit; dark green-colored leaves; mid-season flowering response; under natural season conditions, plants flower in about 8.5 weeks in Southern, California; large inflorescences with very light yellow-colored flower bracts; and good post-production longevity.

1 Drawing Sheet

Botanical designation: *Euphorbia pulcherrima* Willd.
Cultivar denomination: ' OGLPNT14001'.

BACKGROUND OF THE INVENTION

The present invention relates to a new and distinct cultivar of Poinsettia plant, botanically known as *Euphorbia pulcherrima* Willd., and hereinafter referred to by the name 'OGLPNT14001'.

The new Poinsettia plant is a product of a planned breeding program conducted by the Inventor in Lompoc, Calif. The objective of the breeding program is to create new Poinsettia cultivars having large inflorescences, flower bracts with desirable colors, uniform plant habit and excellent post-production longevity.

The new Poinsettia plant originated from a cross-pollination made by the Inventor in December, 1999 of a proprietary selection of *Euphorbia pulcherrima* Willd. identified as code number 99-157-5, not patented, as the female, or seed, parent, with a proprietary selection of *Euphorbia pulcherrima* Willd. identified as code number 98-122-1, not patented, as the male, or pollen, parent. The new Poinsettia plant was discovered and selected by the Inventor as a single flowering plant within the progeny of the stated cross-pollination in a controlled greenhouse environment in Lompoc, Calif. in December, 2000.

Asexual reproduction of the new Poinsettia plant by terminal vegetative cuttings in a controlled greenhouse environment in Lompoc, Calif. since July, 2001, has shown that the unique features of this new Poinsettia plant are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'OGLPNT14001'. These characteristics in combination distinguish 'OGLPNT14001'as a new and distinct cultivar of Poinsettia:

1. Uniform, upright, outwardly spreading and mounded plant habit.
2. Vigorous growth habit.
3. Freely branching habit.
4. Dark green-colored leaves.
5. Mid-season flowering response; under natural season conditions, plants flower in about 8.5 weeks in Southern, California.
6. Large inflorescences with very light yellow-colored flower bracts.
7. Good post-production longevity.

In side-by-side comparisons conducted in Encinitas, Calif., plants of the new Poinsettia differed from plants of the female parent selection in the following characteristics:

1. Leaves of plants of the new Poinsettia are slightly lighter in color than leaves of plants of the female parent selection.
2. Plants of the new Poinsettia flower earlier than plants of the female parent selection.
3. Plants of the new Poinsettia and the female parent selection differ in flower bract color as plants of the female parent selection have greenish white-colored flower bracts.

In side-by-side comparisons conducted in Encinitas, Calif., plants of the new Poinsettia differed from plants of the male parent selection in the following characteristics:

1. Leaves of plants of the new Poinsettia are slightly darker in color than leaves of plants of the male parent selection.
2. Plants of the new Poinsettia and the male parent selection differ in flower bract color as plants of the male parent selection have creamy white-colored flower bracts.

Plants of the new Poinsettia can be compared to plants of the *Euphorbia pulcherrima* Willd. '490 White', disclosed in U.S. Plant Pat. No. 8,772. In side-by-side comparisons conducted in Encinitas, Calif., plants of the new Poinsettia differed from plants of '490 White' in the following characteristics:

1. Under natural season conditions, plants of the new Poinsettia flowered about one week later than plants of '490 White'.
2. Plants of the new Poinsettia had smaller flower bracts than plants of '490 White'.

BRIEF DESCRIPTION OF THE PHOTOGRAPHS

The accompanying photographs illustrate the overall appearance of the new Poinsettia plant. These photographs show the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet comprises a side perspective view of a typical flowering plant of 'OGLPNT14001' grown in a container.

The photograph at the top of the sheet is a close-up view of typical inflorescences of 'OGLPNT14001'.

DETAILED BOTANICAL DESCRIPTION

Plants used in the aforementioned photographs and the following observations and measurements describe plants grown in Encinitas, Calif. during the autumn and winter in a polyethylene-covered greenhouse and under conditions and cultural practices which approximate those generally used in commercial Poinsettia production. During the production of the plants, day temperatures averaged 25° C., night temperatures averaged 17° C. and light levels averaged 4,000 foot-candles. Measurements and numerical values represent averages for typical flowering plants. Single plants were grown in 16.5-cm containers and were pinched one time. Plants had been growing for 18 weeks when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'OGLPNT14001'.

Parentage:

*Female, or seed, parent.*—Proprietary selection of *Euphorbia pulcherrima* Willd. identified as code number 99-157-5, not patented.

*Male, or pollen, parent.*—Proprietary selection of *Euphorbia pulcherrima* Willd. identified as code number 98-122-1, not patented.

Propagation:

*Type.*—Terminal vegetative cuttings.

*Time to initiate roots.*—About 10 to 14 days at 21° C.

*Time to produce a rooted young plant.*—About four weeks at 21° C.

*Root description.*—Fibrous; white in color.

Plant description:

*Plant habit and form.*—Uniform, upright, outwardly spreading and mounded plant habit; broad inverted triangle; inflorescences positioned above the foliar plane; vigorous growth habit.

*Plant height.*—About 28 cm.

*Plant diameter or spread.*—About 43 cm.

*Lateral branch description.*—Quantity: Freely branching habit, about eight lateral branches develop after pinching. Length: About 26 cm. Diameter: About 5 mm. Internode length: About 2.3 cm. Strength: Strong. Texture: Smooth, glabrous. Color: Close to 146A.

*Foliage description.*—Arrangement: Alternate, simple. Length: About 11.2 cm. Width: About 7.5 cm. Shape: Elliptical with occasional shallow lobes. Apex: Acuminate. Base: Attenuate. Margin: Entire with occasional shallow lobing. Venation pattern: Pinnate, arcuate. Texture, upper surface: Smooth, glabrous. Texture, lower surface: Pubescent. Color: Developing and fully expanded leaves, upper surface: Close to 147A; venation, close to 147C. Developing and fully expanded leaves, lower surface: Close to 146A; venation, close to 147C. Petiole: Length: About 3.2 cm. Diameter: About 2 mm. Texture, upper surface: Smooth, glabrous. Texture, lower surface: Sparsely pubescent. Color, upper surface: Close to 146C. Color, lower surface: Close to 146D.

Inflorescence description:

*Inflorescence type and habit.*—Inflorescences are compound corymbs of cyathia with colored flower bracts subtending the cyathia; inflorescences positioned above the foliage.

*Quantity of inflorescence.*—One inflorescence develops per lateral branch; about eight inflorescences per plant.

*Fragrance.*—Not detected.

*Natural flowering season.*—Plants typically flower during the autumn and winter in Southern California; inflorescence initiation and development can also be induced under artificial long nyctoperiod/short photoperiod conditions; mid-season flowering habit, plants flower about 8.5 weeks under natural season conditions in Southern California.

*Post-production longevity.*—Good post-production longevity; plants of the new Poinsettia maintain good substance and bract color for about four weeks under interior conditions; inflorescences persistent.

*Inflorescence size.*—Diameter: Large, about 30 cm. Height (depth): About 10 cm.

*Flower bracts.*—Quantity per inflorescence: About 22. Length, largest bracts: About 12.7 cm. Width, largest bracts: About 9 cm. Shape: Elliptical with irregular shallow lobes. Apex: Acuminate. Base: Attenuate. Margin: Entire with irregular shallow lobing. Texture, upper and lower surfaces: Smooth, glabrous. Venation pattern: Pinnate, arcuate. Color: Developing or transitional bracts, upper surface: Close to 1D; venation, close to 146A. Developing or transitional bracts, lower surface: Close to 4D; venation, close to 146C. Fully expanded bracts, upper surface: Close to 8D; venation, close to 8D; color becoming closer to 2D with development. Fully expanded bracts, lower surface: Close to 4D; venation, close to 4D; color becoming closer to 2D with development. Bract petiole: Length: About 2.8 cm. Diameter: About 2 mm. Texture, upper and lower surfaces: Smooth, glabrous. Color, upper and lower surfaces: Close to 145C.

*Cyathia.*—Quantity per corymb: About 18. Length: About 1.3 cm. Width: About 6 mm. Shape: Ovoid. Color, immature: Close to 146D. Color, mature: Close to N144C. Nectaries: Quantity per cyathium: One.

Length: About 3.5 mm. Diameter: About 3 mm. Shape: Elliptical to ovoid. Color: Close to 12A.

*Peduncles.*—Length: About 4 mm. Diameter: About 2 mm. Strength: Strong. Aspect: Mostly upright. Texture: Smooth, glabrous. Color: Close to 145A.

*Reproductive organs.*—Stamens: Quantity per cyathium: About ten to twelve. Filament length: About 5 mm. Filament color: Close to 157D. Anther shape: Bi-lobed. Anther length: About 1 mm. Anther color: Close to 153C. Amount of pollen: Scarce. Pollen color: Close to 1B. Pistils: Quantity per cyathium: One or two. Pistil length: About 1 cm. Stigma shape: Six-parted. Stigma color: Close to 151D. Style length: About 4 mm. Style color: Close to 145C. Ovary color: Close to 144A. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 16° C. to about 29° C.

It is claimed:

1. A new and distinct Poinsettia plant named 'OGLPNT14001' as illustrated and described.

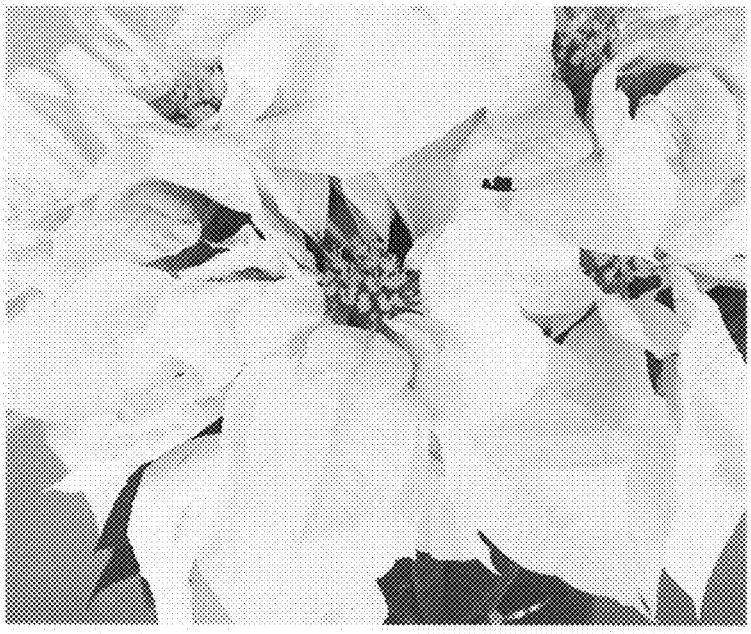
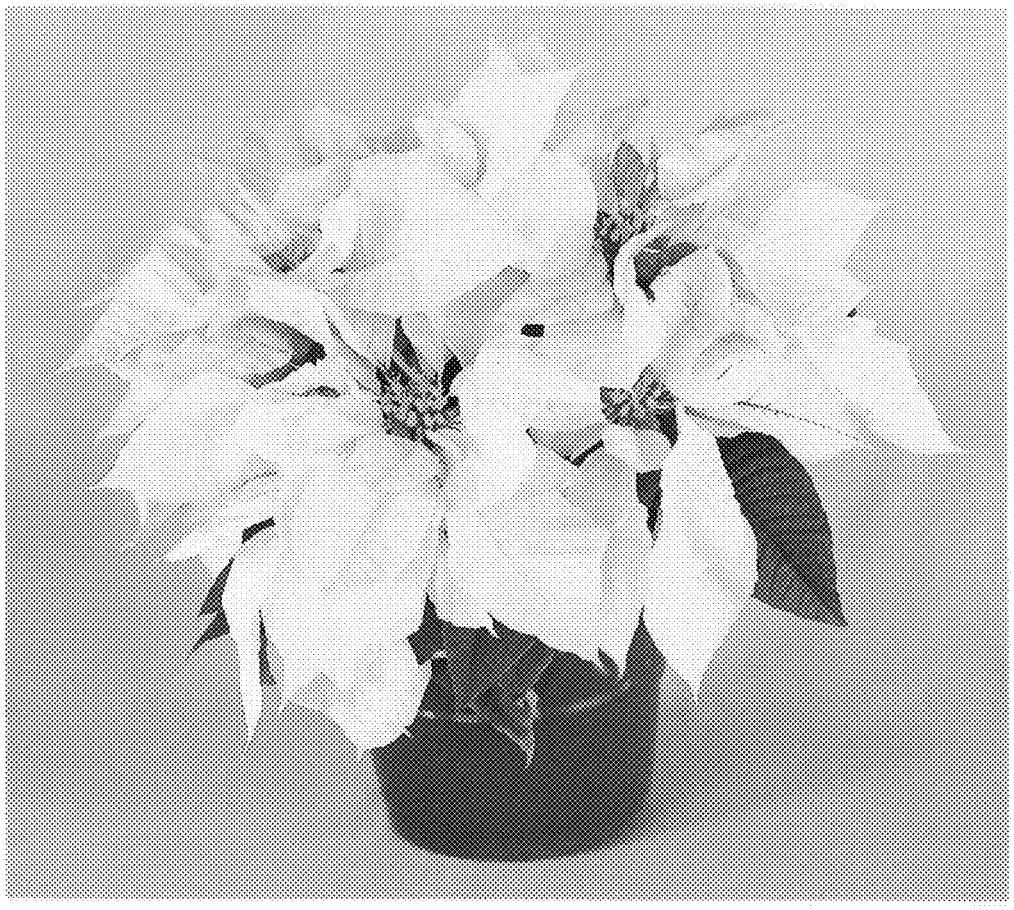

* * * * *